United States Patent [19]

Winters et al.

[11] 4,113,731
[45] Sep. 12, 1978

[54] FUSED ISOQUINOLINE DERIVATIVES

[75] Inventors: Giorgio Winters; Nunzio DiMola, both of Milan, Italy

[73] Assignee: Gruppo Lepetit S.p.A., Milan, Italy

[21] Appl. No.: 713,011

[22] Filed: Aug. 9, 1976

[30] Foreign Application Priority Data

Aug. 27, 1975 [IT] Italy ................... 26591/75

[51] Int. Cl.² ................ C07D 471/14; C07D 495/14; C07D 513/14
[52] U.S. Cl. .................. 260/288 CF; 260/283 S; 260/289 C; 424/258
[58] Field of Search ....... 260/288 CF, 283 S, 283 SY, 260/289 C

[56] References Cited

U.S. PATENT DOCUMENTS

| | | | |
|---|---|---|---|
| 3,630,745 | 12/1971 | Beavers et al. | 96/109 |
| 3,644,366 | 2/1972 | Jeanmart et al. | 260/286 R |
| 3,663,551 | 5/1972 | Deryckere et al. | 260/283 SY |

FOREIGN PATENT DOCUMENTS 472,938  6/1975  U.S.S.R. ................ 260/288 CF

OTHER PUBLICATIONS

Goodman et al, The Pharmacological Basis of Therapeutics (1965) pp. 37–43.
Bailey et al., Chemical Abstracts 51 417a (1957).
Ried et al., Chemical Abstracts, 64, 695a (1966).
Mohunta et al., J. Chem. Soc. (1934), pp. 1263–1264.
Winters et al., Chemical Abstracts, vol. 84, 43,930e (1976) of paper in Tetrahedron Letters (44) 3877–3878 (1975).

*Primary Examiner*—Donald G. Daus
*Assistant Examiner*—Diana G. Rivers
*Attorney, Agent, or Firm*—Theodore Post; C. Kenneth Bjork; Daniel L. DeJoseph

[57] ABSTRACT

Fused isoquinoline derivatives of the general formula

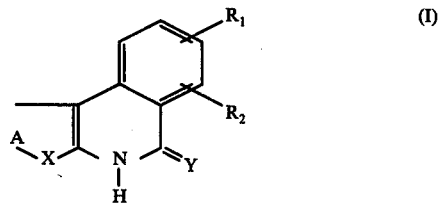

wherein: A is a divalent radical selected from the groups

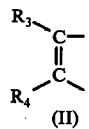 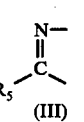 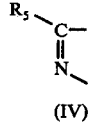

wherein $R_3$ and $R_4$ each independently represents hydrogen, alkyl, alkenyl, cycloalkyl, aryl, aralkyl, aralkenyl, cycloalkyl-alkyl or, taken together with the adjacent double bond, represent a cycloalkene containing from 5 to 8 carbon atoms or an aromatic nucleus;

$R_5$ represents hydrogen, hydroxyl, alkyl, alkenyl, cycloalkyl, aryl, aralkyl, aralkenyl or cycloalkyl-alkyl;

Y is =O, =S or =NH;

X is —O—, —S— or —NR$_6$— wherein $R_6$ represents hydrogen, alkyl, cycloalkyl, aryl, aralkyl or cycloalkyl-alkyl;

$R_1$ and $R_2$ each independently represents hydrogen, alkyl, phenyl, cycloalkyl, alkoxy, alkenyloxy, methylenedioxy, cycloalkoxy, halo or di-alkylamino or, taken together with the adjacent carbon atoms of the benzene ring, form a cycloalkenyl group containing 5 or 6 carbon atoms or an aromatic nucleus fused on the benzene ring. The compounds are essentially prepared through thermal cyclization of a compound of the formula

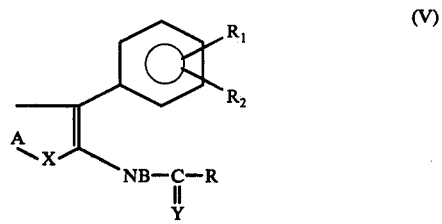

wherein A, X, Y, $R_1$ and $R_2$ have the same meanings given before, with the proviso that $R_1$ and $R_2$ cannot simultaneously occupy both the ortho positions, B represents hydrogen, R represents an —OR$_7$ or —NR$_8$R$_9$ radical wherein $R_7$ is alkyl, aryl or aralkyl and $R_8$ and $R_9$ each independently represents hydrogen, alkyl, aryl, aralkyl, or taken together with the adjacent nitrogen atom represent a heterocyclic saturated radical of 5 or 6 atoms which may contain a further hetero-atom selected from oxygen and nitrogen, or the symbols B and R taken together represent a further bond between the adjacent carbon and nitrogen atoms.

21 Claims, No Drawings

FUSED ISOQUINOLINE DERIVATIVES

SUMMARY OF THE INVENTION

The present invention relates to a new process for preparing fused isoquinoline derivatives and to the new compounds prepared according to this process. More particularly, the compounds which are prepared according to the process of the present invention are members of the class of fused isoquinoline derivatives having the general formula

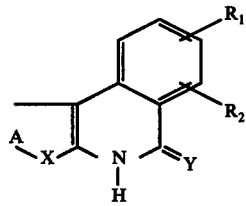

wherein:
A is a divalent radical selected from the groups

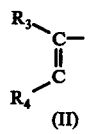 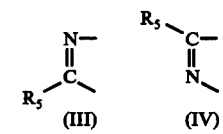 

wherein $R_3$ and $R_4$ each independently represents hydrogen, alkyl, alkenyl, cycloalkyl, aryl, aralkyl, aralkenyl, cycloalkyl-alkyl or, taken together with the adjacent double bond, represent a cycloalkene containing from 5 to 8 carbon atoms or an aromatic nucleus;

$R_5$ represents hydrogen, hydroxyl, alkyl, alkenyl, cycloalkyl, aryl, aralkyl, aralkenyl or cycloalkyl-alkyl;

Y is =O, =S or =NH;

X is —O—, —S— or —$NR_6$— wherein $R_6$ represents hydrogen, alkyl, cycloalkyl, aryl, aralkyl, or cycloalkyl-alkyl;

$R_1$ and $R_2$ each independently represent hydrogen, alkyl, phenyl, cycloalkyl, alkoxy, alkenyloxy, methylenedioxy, cycloalkoxy, halo or di-alkylamino or, taken together with the adjacent carbon atoms or the benzene ring, form a cycloalkenyl group containing 5 or 6 carbon atoms or an aromatic nucleus fused on the benzene ring.

In the specification and claims of the present invention, the term "alkyl" per se or the alkyl moiety of the other substituents listed which contain an aliphatic portion, such as, for instance, "alkoxy", "aralkyl" and "cycloalkyl-alkyl" groups, identifies straight or branched chain radicals containing at most 15 carbon atoms. The term "alkenyl" per se or the alkenyl portion of other substituents above listed, such as, for instance, "alkenyloxy" or "aralkenyl" groups, identifies straight or branched chain aliphatic radicals containing from 3 to 15 carbon atoms and one or more double bonds. The term "aromatic nucleus", "aryl" or the arylic portion of other groups containing an aromatic moiety identifies benzene or naphthalene radicals per se or having on the ring alkyl, alkenyl, cycloalkyl, phenyl, cyano, trifluoromethyl, nitro, di-alkylamino, halo, alkoxy, carboxy, carbalkoxy, sulfo, sulfamoyl and alkyl-sulfonyl groups. The term "cycloalkyl" per se, or the cycloalkylic portion of other substituents above listed such as "cycloalkyl-alkyl", identifies cycloaliphatic radicals containing from 5 to 8 carbon atoms. The term "halo" represents fluoro, chloro, bromo or iodo.

The process for preparing the compounds of the present invention comprises heating in high boiling inert organic solvents or in mineral oil suspensions or, in the solid state, compounds of the formula

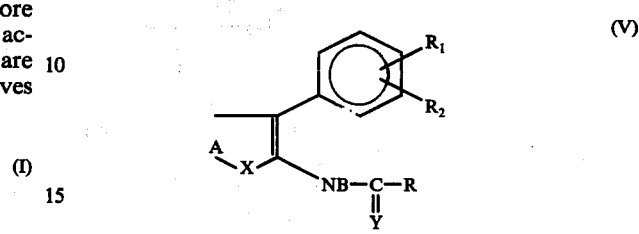

wherein A, X, Y, $R_1$, $R_2$ have the same meanings given before, with the proviso that $R_1$ and $R_2$ cannot simultaneously occupy both the ortho positions, B represents hydrogen, R represents an —$OR_7$ or —$NR_8R_9$ radical wherein $R_7$ is alkyl, aryl or aralkyl and $R_8$ and $R_9$ each independently represents hydrogen, alkyl, aryl, aralkyl or, taken together with the adjacent nitrogen atoms, represent a heterocyclic saturated radical of 5 or 6 atoms which may contain a further hetero-atom selected from oxygen and nitrogen, or the symbols B and R taken together represent a further bond between the adjacent carbon and nitrogen atoms. The starting materials of Formula (V) may be easily obtained from the corresponding amines according to classic methods and common techniques, such as, for instance, reaction with isocyanates or thioisocyanates, or with a suitable carbonyl halide or anhydride.

DESCRIPTION OF SOME PREFERRED EMBODIMENTS

According to a preferred mode of carrying out the process of the invention, the compound of Formula (V) is heated at the solid state or in a mineral oil suspension at a temperature between about 220° C. and about 320° C. and preferably between 240° C. and 310° C. and for a period of time ranging between 1 minute and 2 hours and preferably between 1 minute and 1 hour. The reaction yields vary on the average between about 60 and about 95%.

The thermal cyclization reaction of the present invention is as follows:

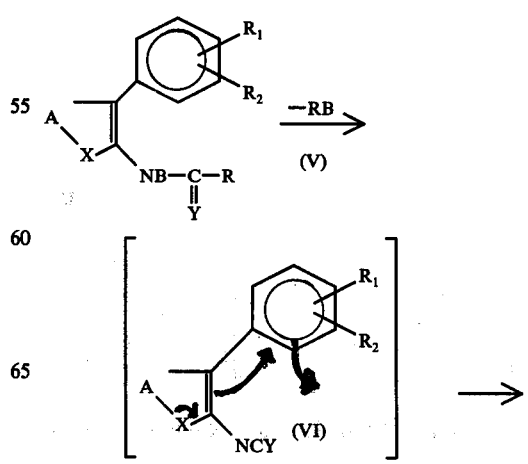

-continued

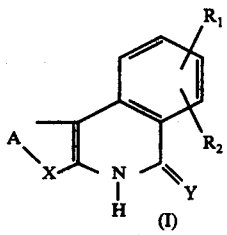

It is obvious that when, in the compound of Formula (V), the symbols B and R taken together represent a further bond between the adjacent carbon and nitrogen atoms, the starting compound identifies itself with the intermediate (VI). It is then understood that any process using a starting material having a formula different from (V), which runs through an intermediate of Formula (VI) to an isoquinoline derivative of Formula (I), falls within the scope of the present invention.

The following processes for preparing compounds of Formula (I), wherein apart from the meaning of the other substituents, Y is oxygen or sulfur, also fall within the scope of the present invention:

(1) Treatment of the corresponding primary amine of Formula (VII)

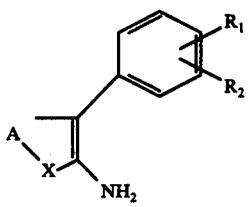

or a salt thereof, wherein A, X, $R_1$ and $R_2$ have the same meaning as before, with the proviso that $R_1$ and $R_2$ cannot simultaneously occupy both the ortho positions of the benzene ring; with phosgene or thiophosgene in inert organic solvents at the boiling temperature of the reaction mixture. The products thus obtained, Formulas (VIII) and (IX),

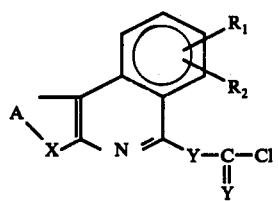

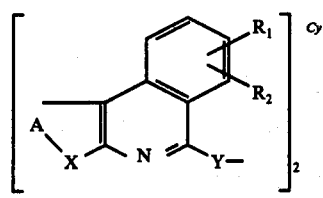

upon hydrolysis afford the desired product of Formula (I).

(2) Heating the amine of Formula (VII) or a salt thereof with an excess of an alkali metal cyanate or thiocyanate.

(3) Heating the amine of Formula (VII) or a salt thereof with urea or thiourea, substituted or not, of formula $NH_2CYNR_8R_9$ wherein Y is =O or =S and $R_8$ and $R_9$ are defined as before.

The compounds of the invention have the following characteristics: high melting points, a very low solubility in common organic solvents such as acetone, lower alkanols, halogenated hydrocarbons and a fair solubility in diethylformamide and in aqueous alcoholic alkali. As regards spectroscopic data, the compounds of the invention are fluorescent under U.V. irradiation; in the I.R. spectrum they show a broad band a 3100–2500 $cm^{-1}$ and another band in the double >C=Y bond region, which demonstrates the presence of a tautomeric equilibrium; and the N.M.R. and Mass Spectra are in complete agreement with the assigned structures.

The inventive compounds are useful as stabilizers in photographic emulsions, as intermediates in the manufacture of dyestuffs for textiles and for photography and as fluorescent and bleaching substances. Moreover, the compound of the following Example 15 is useful as a C.N.S. depressant.

The following additional descripton and examples further describe the invention and the manner and process of making and using it to enable the art skilled to make and use the same and set forth the best mode contemplated by the inventors of carrying out the invention.

EXAMPLE 1

7-Methylindolo[2,3-c]isoquinolin-5(6H)-one

To a solution of 2.59 g (0.01 mole) of 2-amino-1-methyl-3-phenylindole in 15 ml of pyridine, 2.84 g (0.026 mole) of ethylchlorocarbonate is added. The reaction mixture is heated to 75° C. for about 2 hours, allowed to cool and 2.84 g more of ethylchlorocarbonate is added. The reaction mixture, heated for a further 3 hours, is then poured into about 200 ml of aqueous 10% HCl solution, the product is extracted with ethyl ether and the organic layer washed with water. The resulting etheral solution, dried over sodium sulfate, is concentrated to a volume of about 30 ml, 20 ml of hexane is added and the solution is once again concentrated to 35 ml. The product, 2.3 g of 1-methyl-3-phenylindole-2-carbamic acid ethyl ester, is thus crystallized; (m.p. 159°–161° C.; yield 80%). A quantity of 1.4 g of the so obtained carbamate is heated to 270° C. for 15 minutes and the residue crystallized from dimethylformamide, yielding 1.15 g of 7-methylindolo[2,3-c]isoquinolin-5(6H)-one. M.p. 350° C. (with decomposition). Yield 95%.

|  | Microanalysis % Calculated for $C_{16}H_{12}N_2O$ | Found |
|---|---|---|
| C | 77.40 | 77.52 |
| H | 4.87 | 5.01 |
| N | 11.28 | 11.40 |

EXAMPLE 2

7-Methylindolo[2,3-c]isoquinoling-5(6H)-one

The same product as in the foregoing example is prepared by heating to 270°–280° C. for 15 minutes 2.59 g (0.01 mole) of 2-amino-1-methyl-3-phenylindole hydrochloride and 3.24 g (0.04 mole) of KOCN in 25 ml of vaseline oil. The reaction mass is taken up with hexane and the insoluble parts, collected by filtration under vacuum, are washed with water in order to remove inorganic salts and crystallized from dimethylformamide, yielding 0.5 g of the pure desired product.

| | Microanalysis % Calculated for $C_{16}H_{12}N_2O$ | Found |
|---|---|---|
| C | 77.40 | 77.55 |
| H | 4.87 | 4.98 |
| N | 11.28 | 11.17 |

EXAMPLE 3

7-Methylindolo[2,3-c]isoquinolin-5(6H)-one

The same product of Examples 1 and 2 is obtained by heating 0.5 g (about 2 millimole) of 2-amino-1-methyl-3-phenylindole hydrochloride and 0.5 g (50 millimole) of urea to 270° C. for 3 minutes. The residue is taken up with water and filtered, giving 0.6 g of a substance, which, on crystallization from dimethylformamide, yields 0.3 g of the desired product.

| | Microanalysis % Calculated for $C_{16}H_{12}N_2O$ | Found |
|---|---|---|
| C | 77.40 | 77.58 |
| H | 4.87 | 4.92 |
| N | 11.28 | 11.36 |

EXAMPLE 4

1-Methyl-3-phenyl-3H-pyrazolo[3,4-c]isoquinolin-5(4H)-one

A stirred solution of 54.2 g (0.217 mole) of 5-amino-3-methyl-1,4-diphenylpyrazole and 26.05 g (0.224 mole) of phenylisocyanate in 540 ml of anhydrous benzene is heated to 55°-60° C. for 5 hours in an apparatus sheltered from humidity. The reaction mixture is allowed to stand overnight and the precipitate is then filtered and washed with ethyl ether. A quantity of 66.2 g of the corresponding phenylurea derivative, crystallized from ethanol, is obtained (m.p. 217°-224° C.; yield 83%) and is fused by dipping the product-containing vessel into a metal bath at 270°-280° C.

The product first melts, after some minutes aniline begins to distil and finally the melted product solidifies. In crystallization from dimethylformamide 42 g of the desired product is obtained. M.p. 302°-304° C.; yield 85%.

| | Microanalysis % Calculated for $C_{17}H_{13}N_3O$ | Found |
|---|---|---|
| C | 75.55 | 75.55 |
| H | 5.38 | 5.47 |
| N | 16.02 | 16.06 |

EXAMPLE 5

2-(p-Tolyl)thiazolo[5,4-c]isoquinolin-5-(4H)-one

To a solution of 1.33 g (5 millimole) of 5-amino-2-(p-tolyl)-4-phenylthiazole in 45 ml of benzene, 0.9 g (7.5 millimole) of the phenylisocyanate in 5 ml of anhydrous benzene is added at room temperature. The reaction mixture is refluxed for 3 hours and 0.45 g (3.75 millimole) of additional phenylisocyanate is added, refluxing is continued for an additional 3 hours, the reaction mixture is cooled and the insoluble part recovered by filtration under vaccum and washed with benzene. On crystallization from ethanol, 1.5 g of the corresponding phenylurea is obtained (M.p. 247°-263° C.; yield 78%). 25 Grams of the resulting 1-phenyl-3-[4-phenyl-2-(p-tolyl)-thiazol-5-yl]urea is heated on a metal bath to a temperature of 300°-305° C.; until aniline distills which, on condensing, dissolves phenylurea which has previously sublimed. After some minutes, the reaction mass is cooled and ethyl acetate-ethyl ether mixture is added thereto. On filtering under vacuum, a substance is recovered which, on crystallization from dimethylformamide, gives 19 g of the desired product (m.p. 314°-316° C.; yield 75%).

| | Microanalysis % Calculated for $C_{17}H_{12}N_2OS$ | Found |
|---|---|---|
| C | 69.84 | 69.46 |
| H | 4.14 | 4.02 |
| N | 9.58 | 9.45 |
| S | 10.97 | 10.80 |

EXAMPLE 6

2,3-Dimethoxy-7-methyl-7H-indolo[2,3-c]-isoquinolin-5(6H)-one

To a suspension of 15.9 g (0.05 mole) of 2-amino-3-(3,4-dimethoxyphenyl)-1-methylindole in 250 ml of ethyl acetate, 100 ml of 1N NaOH is added. The organic layer is extracted, washed with water, dried over sodium sulfate and then over molecular sieve 3 A.

To this solution, kept under a nitrogen atmosphere, 9 g (0.75 mole) of phenylisocyanate is added at room temperature. The solution is then refluxed for 3 hours, cooled to 0° C. and filtered. The insoluble part, crystallized from acetone, yields 4.1 g of the corresponding phenylurea derivative. M.p. 200° C.

The phenylurea derivative thus obtained, following the procedure of Example 4, is heated to 280° C. for 15 minutes, giving the desired product in a 95% yield. M.p. >310° C.

| | Microanalysis % Calculated for $C_{18}H_{16}N_2O_3$ | Found |
|---|---|---|
| C | 70.11 | 69.61 |
| H | 5.23 | 5.38 |
| N | 9.09 | 8.87 |

EXAMPLE 7

3-Isopropyl-7-methyl-7H-indolo[2,3-c]-isoquinolin-5(6H)-one

The title compound is obtained following the procedure of the foregoing example, heating 3-[1-methyl-3-(4-isopropylphenyl)-indol-2-yl]-1-phenylurea (m.p. 212°-215° C.) for 15 minutes to 290° C. M.p. 315°-325° C.; yield 93%.

| | Microanalysis % Calculated for $C_{19}H_{18}N_2O$ | Found |
|---|---|---|
| C | 78.59 | 78.70 |

-continued

| | Microanalysis % Calculated for $C_{19}H_{18}N_2O$ | Found |
|---|---|---|
| H | 6.25 | 6.35 |
| N | 9.65 | 9.51 |

EXAMPLE 8

3,7-Dimethyl-7H-indolo[2,3-c]isoquinolin-5(6H)-one

The title compound is obtained following the procedure of Example 6, heating 3-[1-methyl-3-(p-tolyl)-indol-2-yl]-1-phenylurea (m.p. 240° C.) for 15 minutes to 290° C. M.p. >310° C.; yield 90%.

| | Microanalysis % Calculated for $C_{17}H_{14}N_2O$ | Found |
|---|---|---|
| C | 77.84 | 77.78 |
| H | 5.83 | 5.60 |
| N | 10.68 | 10.50 |

EXAMPLE 9

3-Methoxy-7-methyl-7H-indolo[2,3-c]-isoquinolin-5(6H)-one

The title compound is prepared following the procedure of Example 6, heating 3-[1-methyl-3-(4-methoxyphenyl)indol-2yl]-1-phenylurea (m.p. 250° C. for 15 minutes to 290° C. M.p. >310° C.; yield 91%.

| | Microanalysis % Calculated for $C_{17}H_{14}N_2O_2$ | Found |
|---|---|---|
| C | 73.36 | 73.11 |
| H | 5.07 | 5.10 |
| N | 10.07 | 9.90 |

EXAMPLE 10

3-Chloro-7-methyl-7H-indolo[2,3-c]isoquinolin-5(6H)-one

The title compound is prepared following the procedure of Example 6, heating 3-[1-methyl-3-(4-chlorophenyl)-indol-2-yl]-1-phenylurea (m.p. 300° C.) for 30 minutes to 250° C. M.p. >310° C.; yield 77%.

| | Microanalysis % Calculated for $C_{16}H_{11}ClN_2O$ | Found |
|---|---|---|
| C | 67.97 | 68.13 |
| H | 3.92 | 3.93 |
| N | 9.91 | 9.84 |
| Cl | 12.54 | 12.46 |

EXAMPLE 11

1,3-Dimethyl-3H-pyrazolo[3,4-c]isoquinolin-5(4H)-one

To 42.6 g (0.228 mole) of 5-amino-1,3-dimethyl-4-phenyl-3H-pyrazolo in 450 ml of benzene and 170 ml of anhydrous ethyl acetate, 30 g (0.252 mole) of phenylisocyanate is gradually added with stirring at room temperature. The reaction mixture is heated to 60° C. for 4 hours, cooled and the precipitate which forms is filtered under vacuum and washed with ethyl ether, giving 69 g of the corresponding phenylurea derivative (m.p. 200°-204° C.).

10 Grams of this compound is melted at 280° C. for 10 minutes and the residue is crystallized from dimethylformamide, giving 6.2 g of the desired product. M.p. >310° C.; yield 89%.

| | Microanalysis % Calculated for $C_{12}H_{11}N_3O$ | Found |
|---|---|---|
| C | 67.59 | 67.65 |
| H | 5.20 | 5.44 |
| N | 19.71 | 19.61 |

EXAMPLE 12

3-Phenyl-3H-pyrazolo[3,4-c]isoquinolin-5(4H)-one

7 Grams of 3-[1,4-diphenyl-pyrazol-5-yl]-1-phenylurea prepared following the procedure of the foregoing example, is melted at 280° C. for 5 minutes. The melted mass is then allowed to cool and is crystallized from dimethylformamide, giving 3.7 g of the pure desired product. M.p. 284°-286° C.; yield 75%.

| | Microanalysis % Calculated for $C_{16}H_{11}N_3O$ | Found |
|---|---|---|
| C | 73.55 | 73.20 |
| H | 4.24 | 4.33 |
| N | 16.05 | 16.22 |

EXAMPLE 13

1,3-Dimethyl-3H-pyrazolo[3,4-c]isoquinolin-5-(4H)-one

The compound of Example 11 is also obtained in the following way: To 1.87 g (10 millimole) of 5-amino-1,3-dimethyl-4-phenyl-3H-pyrazole suspended in 20 ml of benzene and 10 ml of ethyl acetate, 0.75 g (10.6 millimole) of ethylisocyanate in 5 ml of benzene is added. The reaction is gradually heated to 80° C. and is kept at this temperature for 3 hours. Then it is cooled and the precipitate is filtered, washed with benzene and dried to give 1.25 g of the corresponding ethylurea derivative (m.p. 199°-201° C.). 0.5 Grams of this derivative is melted at 300° C. for 1 minute using an infrared lamp. The melted mass is then allowed to cool and is crystallized from dimethylformamide, giving 0.3 g of the desired product. M.p. >320° C.; yield 70%.

| | Microanalysis % Calculated for $C_{12}H_{11}N_3O$ | Found |
|---|---|---|
| C | 67.59 | 67.50 |
| H | 5.20 | 5.08 |
| N | 19.71 | 19.70 |

EXAMPLE 14

7H-indolo[2,3-c]isoquinolin-5(6H)-one

29 Grams of 3-phenyl-2-(3-phenylureido)-indole, (m.p. 210°-212° C.), obtained by following the procedure of Example 6, is heated to 240° C. for 1 hour. The residue, crystallized from dimethylformamide by adding methanol, gives 14.9 g of the desired product. M.p. >310° C.; yield 72%,

| | Microanalysis % Calculated for $C_{15}H_{10}N_2O$ | Found |
|---|---|---|
| C | 76.91 | 76.85 |
| H | 4.30 | 4.49 |
| N | 11.96 | 11.90 |

EXAMPLE 15

2-Methylthiazolo[5,4-c]isoquinolin-5(4H)-one

1-Phenyl-3-(4-phenyl-2-methylthiazol-5-yl)urea (m.p. 199°–201° C.) obtained by following the procedure described in Example 5, is heated to 300° C. for 3 minutes, giving the desired product in a 55% yield. M.p. 310°–320° C.

| | Microanalysis % Calculated for $C_{11}H_8N_2OS$ | Found |
|---|---|---|
| C | 61.09 | 61.13 |
| H | 3.73 | 3.78 |
| N | 12.95 | 12.85 |
| S | 14.82 | 14.71 |

EXAMPLE 16

2-Ethylthiazolo[5,4-c]isoquinolin-5(4H)-one 4.4 Grams of 3-(2-ethyl-4-phenyl-thiazol-5-yl)-1-phenylurea (m.p. 171°–173° C.), obtained following substantially the procedure described in the first part of Example 5, is gradually heated to 250° C. by means of an electric heater and is maintained at this temperature for about 5 minutes. Then aniline which forms is driven off by distillation under vacuum and the product which crystallizes is sludged with acetone. On crystallization from hot dimethylformamide, 1.6 g of the title compound is obtained. M.p. 254°–257° C.; yield 51%.

| | Microanalysis % Calculated for $C_{12}H_{10}N_2OS$ | Found |
|---|---|---|
| C | 62.59 | 63.05 |
| H | 4.38 | 4.40 |
| N | 12.16 | 12.04 |
| S | 13.92 | 13.60 |

EXAMPLE 17

2-n-Butylthiazolo[5,4-c]isoquinolin-5(4H)-one

15 Grams of 3-(2-n-butyl-4-phenylthiazol-5-yl)-1-phenylurea (m.p. 158°–160° C.), prepared according to the procedure described in the first part of Example 5, is gradually heated to 270° C. and maintained at this temperature for about 5 minutes. Then the reaction mixture is allowed to cool to about 220° C. and aniline which forms is distilled under vacuum. The oily residue on cooling crystallizes, and is sludged with a small amount of hot methanol, giving 8.5 g of the title compound which is then crystallized from ethanol. M.p. 172°–173° C.; yield 54%.

| | Microanalysis % Calculated for $C_{14}H_{14}N_2OS$ | Found |
|---|---|---|
| C | 65.09 | 65.19 |
| H | 5.46 | 5.36 |
| N | 10.84 | 10.72 |

-continued

| | Microanalysis % Calculated for $C_{14}H_{14}N_2OS$ | Found |
|---|---|---|
| S | 12.41 | 12.28 |

EXAMPLE 18

1-Ethyl-3-methyl-3H-pyrazolo[3,4-c]isoquinolin-5(4H)-one

15 Grams of 3-(3-ethyl-1-methylpyrazol-5-yl)-1-phenylurea (m.p. 167°–177° C.), prepared according to the procedure described in the first part of Example 5, is heated to 250° C. for about 2 minutes. Then the reaction mass is cooled and taken up with methanol. On filtering under vacuum and crystallizing from dimethylformamide, 6.6 g of the title compound is obtained. M.p. 291°–294° C.; yield 62%.

| | Microanalysis % Calculated for $C_{13}H_{13}N_3O$ | Found |
|---|---|---|
| C | 68.70 | 68.69 |
| H | 5.77 | 5.82 |
| N | 18.49 | 18.57 |

EXAMPLE 19

2-Phenylthiazolo[5,4-c]isoquinolin-5(4H)-one 15 Grams of crude 3-(2,4-diphenylthiazol-5-yl)-1-phenylurea (m.p. 240°–260° C.), prepared following substantially the procedure described in the first part of Example 5, is heated to 300° C. on a metal bath and maintained at this temperature for about 8 minutes. The reaction mass is then cooled and sludged with ethyl acetate. On crystallization from dimethylformamide, 6.95 g of the title compound is obtained. M.p. >310° C.; yield 62%.

| | Microanalysis % Calculated for $C_{16}H_{10}N_2OS$ | Found |
|---|---|---|
| C | 69.04 | 68.89 |
| H | 3.62 | 3.75 |
| N | 10.06 | 9.90 |
| S | 11.52 | 11.44 |

EXAMPLE 20

1-Hydroxy-3-phenyl-3H-pyrazolo[3,4-c]isoquinolin-5(4H)-one 2.51 Grams (0.01 mole) of 5-amino-3-hydroxy-1,4-diphenylpyrazole is mixed with 1.62 ml (0.015 mole) of phenylisocyanate and is gradually heated to 290° C. The obtained residue is then ground and boiled with 40 ml of ethyl acetate. 2.7 Grams of crude compound recovered by filtering the hot mixture is taken up with aqueous 4% NaOH. On acidifying the filtered solution with acetic acid, 2.24 g of the title compound precipitates. Yield 81%.

| | Microanalysis % Calculated for $C_{16}H_{11}N_3O_2$ | Found |
|---|---|---|
| C | 69.30 | 69.32 |
| H | 4.00 | 4.20 |

-continued

| Microanalysis % Calculated for $C_{16}H_{11}N_3O_2$ | Found |
|---|---|
| N 15.16 | 14.96 |

The following compounds are prepared pursuant to the method of Example 12.

3H-Pyrazolo[3,4-c]isoquinolin-5(4H)-one, m.p. 344°–346° C.

The corresponding 1-methyl derivative of the last-named compound has an m.p. higher than 310° C., and the corresponding 3-methyl derivative has an m.p. higher than 300° C.

What is claimed is:

1. A compound of following Formula (I)

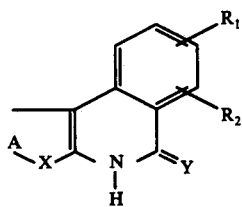

wherein:

A is a divalent radical selected from the groups:

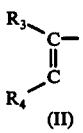 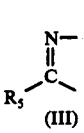 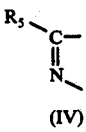
(II)　　(III)　　(IV)

wherein $R_3$ and $R_4$ taken together with the adjacent C═C double bond, represent an unsubstituted benzene ring or a benzene ring substituted with a $C_1$–$C_{15}$ alkyl, $C_3$–$C_{15}$ alkenyl, phenyl, cyano, trifluoromethyl, nitro, sulfo or a sulfamoyl group;

$R_5$ represents hydrogen, hydroxyl, $C_1$–$C_{15}$ alkyl or an unsubstituted phenyl group or a phenyl group substituted with a $C_1$–$C_{15}$ alkyl, $C_3$–$C_{15}$ alkenyl, phenyl, cyano, trifluoromethyl, nitro, sulfo or a sulfamoyl group;

Y is O;

X is S or $NR_6$ wherein $R_6$ represents hydrogen, $C_1$–$C_{15}$ alkyl or an unsubstituted phenyl group or a phenyl group substituted with a $C_1$–$C_{15}$ alkyl, $C_3$–$C_{15}$ alkenyl, phenyl, cyano, trifluoromethyl, nitro, sulfo or a sulfamoyl group;

$R_1$ and $R_2$ each independently represents hydrogen, $C_1$–$C_{15}$ alkyl, alkoxy or halo.

2. The compound of claim 1 which is 7-methylindolo[2,3-c]isoquinolin-5(6H)-one.

3. The compound of claim 1 which is 1-methyl-3-phenyl-3H-pyrazolo[3,4-c]isoquinolin-5(4H)-one.

4. The compound of claim 1 which is 2-(p-tolyl)-thiazolo[5,4-c]isoquinolin-5(4H)-one.

5. The compound of claim 1 which is 7-methyl-2,3-dimethoxy-7H-indolo[2,3-c]isoquinolin-5(6H)-one.

6. The compound of claim 1 which is 3-isopropyl-7-methyl-7H-indolo[2,3-c]isoquinolin-5(6H)-one.

7. The compound of claim 1 which is 3,7-dimethyl-7H-indolo[2,3-c]isoquinolin-5(6H)-one.

8. The compound of claim 1 which is 7-methyl-3-methoxy-7H-indolo[2,3-c]isoquinolin-5(6H)-one.

9. The compound of claim 1 which is 3-chloro-7-methyl-7H-indolo[2,3-c]isoquinolin-5(6H)-one.

10. The compound of claim 1 which is 1,3-dimethyl-3H-pyrazolo[3,4-c]isoquinolin-5(4H)-one.

11. The compound of claim 1 which is 3-phenyl-3H-pyrazolo[3,4-c]isoquinolin-5-(4H)-one.

12. The compound of claim 1 which is 7H-indolo[2,3-c]isoquinolin-5(6H)-one.

13. The compound of claim 1 which is 2-methyl-thiazolo[5,4-c]isoquinolin-5(4H)-one.

14. The compound of claim 1 which is 2-ethyl-thiazolo[5,4-c]isoquinolin-5(4H)-one.

15. The compound of claim 1 which is 2-n-butyl-thiazolo[5,4-c]isoquinolin-5(4H)-one.

16. The compound of claim 1 which is 1-ethyl-3-methyl-3H-pyrazolo[3,4-c]isoquinolin-5(4H)-one.

17. The compound of claim 1 which is 2-phenyl-thiazolo[5,4-c]isoquinolin-5(4H)-one.

18. The compound of claim 1 which is 1-hydroxy-3-phenyl-3H-pyrazolo[3,4-c]isoquinolin-5(4H)-one.

19. The compound of claim 1 which is 3H-pyrazolo[3,4-c]isoquinolin-5(4H)-one.

20. The compound of claim 1 which is 1-methyl-3H-pyrazolo[3,4-c]isoquinolin-5(4H)-one.

21. The compound of claim 1 which is 3-methyl-3-H-pyrazolo[3,4-c]isoquinolin-5(4H)-one.

* * * * *

UNITED STATES PATENT AND TRADEMARK OFFICE
CERTIFICATE OF CORRECTION

PATENT NO. : 4,113,731
DATED : September 12, 1978
INVENTOR(S) : Giorgio Winters, et al.

It is certified that error appears in the above-identified patent and that said Letters Patent are hereby corrected as shown below:

Column 2 of TITLE PAGE, line 2 below formulas II, III and IV, omit second comma after "alkyl";

Column 1, line 45, "atoms or the" should read -- atoms of the --;

Column 2, line 24, "atoms" should read -- atom --;

Column 4, line 16, ">C=Y" should read -- $\geq$C=Y --;

Column 4, line 24, "of the following" should read --of following--;

Column 4, line 26, "descripton" should read --description--;

Column 4, line 65, "isoquinoling" should read --isoquinolin--;

Column 7, line 30, "2yl" should read -- 2-yl --;

Column 7, line 60, "pyrazolo" should read -- pyrazole --;

Column 9, line 29, "4.4" should begin a new paragraph;

Column 10, line 30, "15" should begin a new paragraph;

UNITED STATES PATENT OFFICE
CERTIFICATE OF CORRECTION

Patent No. 4,113,731  Dated September 12, 1978

Inventor(s) Giorgio Winters, et al.

It is certified that error appears in the above-identified patent and that said Letters Patent are hereby corrected as shown below:

Column 12, line 21, "3-H" should read -- 3H --.

Signed and Sealed this

Ninth Day of January 1979

[SEAL]

Attest:

RUTH C. MASON
*Attesting Officer*

DONALD W. BANNER
*Commissioner of Patents and Trademarks*